United States Patent [19]

Dewanckele et al.

[11] Patent Number: 5,569,576
[45] Date of Patent: Oct. 29, 1996

[54] PHOTOGRAPHIC MATERIALS CONTAINING POLYMERIC COMPOUNDS

[75] Inventors: Jean-Marie Dewanckele, Drongen; Geert Vercruysse, Kluisbergen, both of Belgium; Ralf Buscher, Lohmar, Germany

[73] Assignee: AGFA-Gevaert, N.V., Mortsel, Belgium

[21] Appl. No.: 395,112

[22] Filed: Feb. 27, 1995

[30] Foreign Application Priority Data

Mar. 11, 1994 [EP] European Pat. Off. .............. 94200639

[51] Int. Cl.$^6$ ...................................................... G03C 1/46
[52] U.S. Cl. .................... 430/502; 430/599; 430/603; 430/609; 430/611; 430/627; 430/629; 430/536
[58] Field of Search .................................... 430/502, 629, 430/627, 611, 609, 603, 599, 536

[56] References Cited

U.S. PATENT DOCUMENTS

| | | | |
|---|---|---|---|
| 3,784,524 | 1/1974 | Morgan | 528/75 |
| 3,860,428 | 1/1975 | Ponticello et al. | 430/629 |
| 3,986,877 | 10/1976 | Timmerman et al. | 430/599 |
| 4,013,471 | 3/1977 | Pollet et al. | 430/629 |
| 4,292,400 | 9/1981 | Pollet et al. | 430/383 |
| 4,551,421 | 11/1985 | Sugimoto et al. | 430/603 |

Primary Examiner—Geraldine Letscher
Attorney, Agent, or Firm—Breiner & Breiner

[57] ABSTRACT

A photographic material is disclosed containing on at least one side of the support at least one light-sensitive silver halide emulsion layer characterised in that the light-sensitive layer and/or at least one non-light sensitive layer in water-permeable relationship with the light-sensitive layer comprises at least one compound having the general formula (I)

$$R[O-CH_2-CH_2-S-(LINK^1-S)_x-CH_2-CH_2-O-(LINK^2)]_y-OR \quad (I)$$

wherein each of LINK$^1$ and LINK$^2$ which may be the same or different represents a divalent linking group; R represents H, a substituted or unsubstituted alkyl group, a substituted or unsubstituted aryl group or an acyl group; x is 0, 1 or 2, and y varies from 2 to 20.

8 Claims, No Drawings

PHOTOGRAPHIC MATERIALS CONTAINING POLYMERIC COMPOUNDS

DESCRIPTION

1. Field of the Invention

This invention relates to compounds increasing the sensitivity of silver halide emulsion grains coated on photographic elements.

2. Background of the Invention

In most applications in the field of black-and-white as well as in colour photography silver halide emulsion grains giving an increased sensitivity at a smaller particle size are preferred. This is related to the remaining actual demand to get photographic materials that can be processed in shorter processing times and to get images with an outstanding image quality.

Improvements in the preparation methods of silver halide emulsion crystals have contributed to a large extent to reach this goal. So, for non-spectrally sensitised emulsions miscellaneous preparation methods have been worked out in order to provide optimised sensitometric characteristics that can be correlated to the volume of said crystals as has been described, e.g., in EP-A 382 950 and EP-A 528 480. For spectrally sensitised silver halide emulsion crystals a large number of patent applications and patent specifications has been published during the last decade. Especially the preparation, the chemical and spectral sensitisation of tabular silver halide grains with varying aspect ratios for use in various application fields of photography have been proposed.

Optimisation of the chemical ripening, as has been described, e.g., in EP-A 610 609, may lead to still further improvements. Optimisation of the stabilisation as in the cited EP-A 528 480 or of the spectral sensitisation, making use of a supersensitiser, may have an analogous effect. Also the use of development-accelerating compounds is well-known as has been described, e.g., in DE 2 360 878. Therein polyethylene compounds carrying thioether groups as substituents on the linear chain have been described for accelerating or activating the development of exposed silver halide elements.

However, translation of the improved sensitivities and/or gradations in terms of more rapid processing and/or improved image quality can only be maintained if the properties of the film material are preserved during storage, before exposure of the film material. Higher gradations mentioned hereinbefore are, e.g., desired for radiographic materials comprising tabular grains that have a lack in homogeneity of the silver halide grain distribution as advanced preparation methods are required to get satisfying results.

Especially if development accelerators are used disadvantageous effects may appear in that the potential sensitometric properties rapidly deteriorate after coating. Fog increase, e.g., is often met with accelerators carrying thioether groups.

OBJECT OF THE INVENTION

It is an object of the present invention to enhance the sensitivity of black-and-white or colour photographic materials, which sensitivity can be translated in terms of more rapid processing and/or improved image quality and with an acceptable fog, even after preservation.

Further objects will become apparent from the description hereinafter.

SUMMARY OF THE INVENTION

According to this invention a photographic material is disclosed containing on at least one side of the support at least one light-sensitive silver halide emulsion layer characterised in that the light-sensitive layer and/or at least one non-light sensitive layer in water-permeable relationship with the light-sensitive layer comprises at least one compound having the general formula (I)

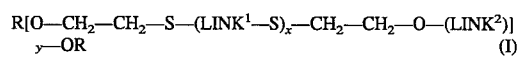

wherein each of $LINK^1$ and $LINK^2$ which may be the same or different represents a divalent linking group; R represents H, a substituted or unsubstituted alkyl group, a substituted or unsubstituted aryl group or an acyl group; x is 0, 1 or 2, and y varies from 2 to 20.

DETAILED DESCRIPTION OF THE INVENTION

According to this invention the compounds having a structure as in formula (I) are polymeric thioethers, which are prepared by an acid-catalysed polycondensation reaction of thiodiglycol with other diol compounds.

The said reaction can be represented, e.g., by the following scheme

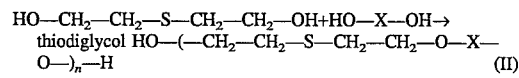

wherein X represents a divalent group like $-CH_2-CH_2-$; $-CH_2-CH_2-O-CH_2-CH_2-$; $(CH_2-CH_2-O)_n-CH_2-CH_2$ with n=1 to 20; $-CH_2-CH_2-CH(CH_3)_2-CH_2-CH_2-$; $-CH_2-CH_2-NH-CO-NH-CH_2-CH_2-$; $-CH_2-C(R^1)(R^2)-CH_2-$; $-CH_2-CH_2-N(COR^3)-CH_2-CH_2-$; $-CH_2-CH_2-NR^4-CH_2-CH_2-$; $-CH_2-Phen-CH_2-$; $-CH_2-CH_2-NH-CO-CO-NH-CH_2-CH_2-$; etc., wherein Phen represents phenyl and each of $R^1$, $R^2$, $R^3$ and $R^4$ independently represents a hydrogen, substituted or unsubstituted alkyl group or a substituted or unsubstituted aryl group.

It is clear that the structures mentioned herein are differing from the "monomeric" structures described, e.g., in EP-B 26 520, in GB 1 163 429 and in U.S. Pat. Nos. 3,997,614 and 4,551,421 as in our invention a polycondensation reaction leads to the preferred "polymeric" structures.

Examples of preferred polymeric compounds corresponding to formula (II) are given hereinafter as compounds C1-C8, wherein X is respectively represented by the following groups $-CH_2-CH_2-O-CH_2-CH_2-$ for compound C1
$-CH_2-CH_2-$ for compound C2
$-(CH_2-CH_2-O)_4-CH_2-CH_2-$ for compound C3
$-CH_2-CH_2-CH_2-$ for compound C4
$-(CH_2-CH_2-O)_3-CH_2-CH_2-$ for compound C5
$-CH_2-CH_2-O-CH_2-CH_2-O-CH_2-CH_2-$ for compound C6
$-(CH_2-CH_2-O)_5-CH_2-CH_2-$ for compound C7
$-CH_2-C(CH_3)_2-CH_2-$ for compound C8

An especially preferred compound according to this invention is compound C7, the preparation of which is given hereinafter.

Preparation of compound C7

In a 3 l reactor, provided with a quickfit bottle holder and a Dean & Stork separator mounted thereon, provided with a multicoil cooling element, 5 moles of diethylene glycol and 5 moles of thiodiethylene glycol were polycondensated in 750 ml of toluene under the influence of a 5 mole % solution of methanesulphonic acid corresponding to an amount of 0.25 mole.

This mixture was refluxed for about 14 h in order to remove an equivalent amount (1.8 mole) of water. The reaction mixture was stirred at room temperature with solid sodium carbonate and filtrated. Then the remaining liquid was evaporated. Yield: about 98%.

Examples of preferred polymeric compounds corresponding to the general formula (I) represented by formula (III)

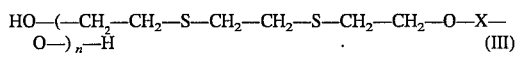

(III)

are given hereinafter as compounds C9-C11, wherein X is respectively represented by the following groups —$CH_2$—$CH_2$—O—$CH_2$—$CH_2$— for compound C9

—$CH_2$—$CH_2$—O—$CH_2$—$CH_2$—O—$CH_2$—$CH_2$— for compound C10

—$(CH_2$—$CH_2$—$O)_6$— for compound C11

- Preferably the compound having a structure corresponding to the general formula (I) is present in the photographic material according to this invention in an amount of 0.1 to 20 mg per square meter and per side of the support that is coated with at least one light-sensitive layer comprising light-sensitive silver halide emulsion crystals.

In another embodiment the compound is present in the protective layer that has been coated over an emulsion layer comprising light-sensitive silver halide or over another non-light-sensitive layer.

The photographic material according to this invention may contain one or more compounds represented by the general formula (I) in at least one silver halide emulsion layer and/or in at least one non-light-sensitive protective layer. The compound(s) may be added to the layer(s) in dissolved or in dispersed form. Suitable solvents should have no harmful effects on the emulsion and preferably should be miscible with water, as ethanol, acetone, pyridine, N,N-dimethylformamide, dimethyl sulphoxide, N-methyl-pyrrolidone, etc.

Said compound(s) may be added at any stage of the emulsion preparation but preferably just before coating. In some cases it may be still more preferable to add the compound(s) by dosage at the coating machine just before the layer(s) is (are) coated on the support.

The silver halide emulsion particles of the photographic emulsions to be coated as light-sensitive layer(s) of the photographic material according to the present invention may have a regular crystalline form such as a cubic or octahedral form or they may have a transition form. They may also have an irregular crystalline form such as a spherical form or a tabular form, or may otherwise have a composite crystalline form comprising a mixture of regular and irregular forms. The silver halide grains may have a multilayered grain structure. According to a simple embodiment the grains may comprise a core and a shell, which may have different halide compositions and/or may have undergone different modifications such as the addition of dopes. Besides having a differently composed core and shell, the silver halide grains may also comprise different phases inbetween.

Two or more types of silver halide emulsions that have been prepared differently, e.g. by mixing the halide and silver solutions in partially or fully controlled conditions of temperature, concentrations, sequence of addition, and rates of addition, according to the single-jet method, the double-jet method, or the conversion method, can be mixed for forming a photographic emulsion for use in a photographic material in accordance with the present invention.

The average size of the silver halide grains may range from 0.1 to 2.0 μm, preferably from 0.2 to 1.0 μm.

The size distribution of the silver halide particles of the photographic emulsions to be used according to the present invention can be homodisperse or heterodisperse. A homodisperse size distribution is obtained when the variation coefficient of the grain size (the ratio of standard deviation of the grain size and the average grain size) is less than 0.25, preferably not more than 0.20 and still more preferably not more than 0.15.

In addition to silver halide the emulsions may also comprise organic silver salts such as, e.g., silver benzotriazolate and silver behenate The silver halide crystals can be doped with $Rh^{3+}$, $Ir^{4+}$, $Cd^{2+}$, $Zn^{2+}$, $Pb^{2+}$, $Ru^{3+}$, $Re^{3+}$.

The photographic emulsions can be prepared from soluble silver salts and soluble halides according to different methods as described e.g. by P. Glafkidès in "Chimie et Physique Photographique", Paul Montel, Paris (1967), by G. F. Duffin in "Photographic Emulsion Chemistry" The Focal Press, London (1966), and by V. L. Zelikman et al in "Making and Coating Photographic Emulsion", The Focal Press, London (1966).

Silver halide grains having a tabular morphology can be prepared as described by Berry et al in Phot. Sci. and Eng., Vol 5, No 6, 1961, by Duffin, Photographic Emulsion Chemistry, Focal Press, 1966, p. 66–72 and in early patent literature including Bogg U.S. Pat. No. 4,063,951, Lewis U.S. Pat. No. 4,067,739 and Maternaghan U.S. Pat. Nos. 4,150,994; 4,184,877 and 4,184,878. However, as the tabular grains described therein cannot be regarded as showing a high diameter-to-thickness ratio, commonly termed aspect ratio, it is more preferable to make use of emulsions having high aspect ratio silver halide crystals as described in the survey thereon which appeared in Research Disclosure, Volume 225, Jan 1983, Item 22534. Preparation methods for the tabular silver halide emulsions used in this invention are described in, e.g., U.S. Pat. No. 4,434,226 (Wilgus et al.) resulting in tabular silver bromoiodide grains having a thickness of less than 0.2 μm, a diameter of at least 0.6 μm and an average aspect ratio greater than 8:1 and accounting for at least 50 percent of the total projected area of all the emulsion grains. Similar tabular emulsion grains can be prepared according to, e.g., U.S. Pat. No. 4,439,520 (Kofron et al) for spectrally sensitised grains; U.S. Pat. No. 4,425,425 (Abbott et al) for radiographic materials containing tabular grains with an aspect ratio of at least 8:1, and U.S. Pat. No. 4,425,426 from the same author for similar grains with an aspect ratio between 5:1 and 8:1. A way can be followed to prepare tabular grains with an increased thickness as described in U.S. Pat. Nos. 4,801,522; 5,028,521 and 5,013,641 using ammonia or ammonia generated "in situ". A more preferred method for the preparation of an emulsion with tabular silver halide grains having an average thickness of less than 0.30 μm and an average aspect ratio of at least 2:1 has been described in EP-Application 569 075.

The emulsion can be desalted in the usual ways, e.g., by dialysis, by flocculation and re-dispersing, or by ultrafiltration.

Two or more types of tabular silver halide emulsions that have been prepared differently can be mixed for forming a photographic emulsion for use in accordance with the present invention. Even mixtures of crystals can be made having a different morphology. Preferred halide compositions for use in photographic materials according to this invention are bromoiodide, chlorobromoiodide, chlorobromide, chloroiodide, bromide and chloride.

The silver halide emulsions in connection with the present invention can be chemically sensitised as described, e.g., in "Chimie et Physique Photographique" by P. Glafkides, in "Photographic Emulsion Chemistry" by G. F. Duffin, in "Making and Coating Photographic Emulsion" by V. L. Zelikman et al, and in "Die Grundlagen der photographischen Prozesse mit Silberhalogeniden" edited by H. Frieser and published by Akademische Verlagsgesellschaft (1968). As described in said literature chemical sensitisation can be carried out by effecting the ripening in the presence of small amounts of compounds containing sulphur e.g. thiosulphate, thiocyanate, thioureas, sulphites, mercapto compounds, and rhodamines. The emulsions may be sensitised also by means of gold-sulphur ripeners or by means of reductors, e.g. tin compounds as described in GB-P 789,823, amines, hydrazine derivatives, formamidine-sulphinic acids, and silane compounds.

The silver halide emulsions may be spectrally sensitised with methine dyes such as those described by F. M. Hamer in "The Cyanine Dyes and Related Compounds", 1964, John Wiley & Sons. Dyes that can be used for the purpose of spectral sensitisation include cyanine dyes, merocyanine dyes, complex cyanine dyes, complex merocyanine dyes, hemicyanine dyes, styryl dyes and hemioxonol dyes. Particularly valuable dyes are cyanine dyes, merocyanine dyes and complex merocyanine dyes. A survey of useful chemical classes of spectral sensitising dyes and specific useful examples in connection with tabular grains is given in the already cited Research Disclosure, Item 22534. Especially preferred green sensitizer in connection with spectrally sensitized emulsion crystals for coating in a photographic element according the present invention are anhydro-5,5'-dichloro-3,3'-bis(n-sulphobutyl)-9-ethyloxacarbo-cyanine hydroxide and anhydro-5,5'-dichloro-3,3'-bis(n-sulphopropyl)-9-ethyloxacarbo-cyanine hydroxide.

In classical emulsion preparation spectral sensitisation traditionally follows the completion of chemical sensitisation. However, in connection with tabular grains, it is specifically considered that spectral sensitisation may occur simultaneously with or may even precede completely the chemical sensitization step: the chemical sensitisation after spectral sensitization is believed to occur at one or more ordered discrete sites of tabular grains as has been described in, e.g., in U.S. Pat. Nos. 4,434,226 and 4,439,520. Emulsions can also be prepared, wherein the chemical sensitisation may further proceed in the presence of one or more phenidones and derivatives, a dihydroxybenzene, e.g. hydroquinone, resorcinol, catechol and/or (a) derivative(s) therefrom, one or more stabilisers or antifoggants, one or more spectral sensitizer(s) or combinations of said ingredients. Especially 1-p-carboxyphenyl-4,4'-dimethyl-3-pyrazolidin-1-one may be added as a preferred auxiliary agent.

The silver halide emulsion layer(s) or the non-light-sensitive layers coated for the preparation of materials according to the present invention may further comprise compounds preventing the formation of fog or stabilising the photographic characteristics during the production or storage of the photographic elements or during the photographic treatment thereof. Many known compounds can be added as fog-inhibiting agents or stabilisers to the silver halide emulsion layer or to other layers in water-permeable relationship therewith such as an undercoat or a protective layer. Suitable examples are, e.g., the heterocyclic nitrogen-containing compounds such as benzothiazolium salts, nitro-imidazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles (preferably 5-methyl-benzotriazole), nitrobenzotriazoles, mercaptotetrazoles, in particular 1-phenyl-5-mercapto-tetrazole, mercaptopyrimidines, mercaptotriazines, benzothiazoline-2-thione, oxazoline-thione, triazaindenes, tetrazaindenes and pentazaindenes, especially those described by Birr in Z. Wiss. Phot. 47 (1952), pages 2–58, triazolopyrimidines such as those described in GB 1,203,757,—1,209,146,—1,500,278, and JA-Appl. 75-39537, and 7-hydroxy-s-triazolo-[1,5-a]-pyrimidines as described in U.S. Pat. No. 4,727,017, and other compounds such as benzenethiosulphonic acid, benzenethiosulphinic acid and benzenethiosulphonic acid amide. Other compounds that can be used as fog-inhibiting compounds are the compounds described in Research Disclosure N° 17643 (1978), Chapter VI. Many of these fog-inhibiting compounds may have been already added during the chemical ripening of the tabular silver halide crystals.

Compounds having a structure corresponding to the general formula (I) according to this invention can be combined with the antifoggants mentioned hereinbefore.

In the preparation of emulsions and in the layer(s) of the photographic material according to the present invention conventional lime-treated or acid-treated gelatin can be used as a protective colloid or as a binder. The preparation of such gelatin types has been described, e.g., in "The Science and Technology of Gelatin", edited by A. G. Ward and A. Courts, Academic Press 1977, page 295 and next pages. The gelatin can also be an enzyme-treated gelatin as described in Bull. Soc. Sci. Phot. Japan, N° 16, page 30 (1966). Before and during the formation of the silver halide grains it is common practice to establish a gelatin concentration of from about 0.05% to 5.0% by weight in the dispersion medium. Additional gelatin is added in a later stage of the emulsion preparation, e.g. after washing, to establish optimal coating conditions and/or to establish the required thickness of the coated emulsion layer. Preferably a ratio by weight of gelatin to silver halide, the silver halide being expressed as equivalent silver nitrate, ranging from 0.3 to 1.0 is then obtained.

The gelatin binder of the photographic elements according to this invention can be prehardened with appropriate hardening agents such as those of the epoxide type, those of the ethylenimine type, those of the vinylsulphone type e.g. divinylsulphonylmethane, ethylene-di-(vinylsulphone), 1,3-vinylsulphonyl-2-propanol, bis-(vinylsulphonyl-methyl)ether, chromium salts, e.g. chromium acetate and chromium alum, aldehydes e.g. formaldehyde, glyoxal, and glutaraldehyde, N-methylol compounds e.g. dimethylolurea and methyloldimethylhydantoine, dioxan derivatives e.g., 2,3-dihydroxy-dioxan, active vinyl compounds, e.g. 1,3,5-triacryloyl-hexahydro-s-triazine, active halogen compounds, e.g. 2,4-dichloro-6-hydroxy-s-triazine, and mucohalogenic acids, e.g. mucochloric acid and mucophenoxychlotic acid. These hardeners can be used alone or in combination. The binder can also be hardened with fast-reacting hardeners such as carbamoylpyridinium salts as disclosed in U.S. Pat. No. 4,063,952 and with the onium compounds as disclosed in EU Patent Application 408,143.

The photographic element of the present invention may further comprise various kinds of surface-active agents in the photographic emulsion layer or in at least one other hydrophilic colloid layer. Suitable surface-active agents include non-ionic agents such as saponins, alkylene oxides e.g. polyethylene glycol, polyethylene glycol/polypropylene glycol condensation products, polyethylene glycol alkyl ethers or polyethylene glycol alkylaryl ethers, polyethylene glycol esters, polyethylene glycol sorbitan esters, polyalkylene glycol alkylamines or alkylamides, silicone-polyethylene oxide adducts, glycidol derivatives, fatty acid esters of polyhydric alcohols and alkyl esters of saccharides; anionic agents comprising an acid group such as a carboxyl, sulpho, phospho, sulphuric or phosphoric ester group; ampholytic agents such as aminoacids, aminoalkyl sulphonic acids, aminoalkyl sulphates or phosphates, alkylbetaines, and amine-N-oxides; and cationic agents such as alkylamine salts, aliphatic, aromatic, or heterocyclic quaternary ammonium salts, aliphatic or heterocyclic cyclic phosphonium or sulphonium salts. Such surface-active agents can be used for various purposes, e.g., as coating aids, as compounds preventing electric charges, as compounds improving slidability, as compounds facilitating dispersive emulsification, as compounds preventing or reducing adhesion, and as compounds improving the photographic characteristics, e.g., higher contrast, sensitisation, and development acceleration. Preferred surface-active coating agents are compounds containing perfluorinated alkyl groups.

The photographic element of the present invention may further comprise various other additives such as e.g. compounds improving the dimensional stability of the photographic element, UV-absorbers, spacing agents and plasticisers.

Suitable additives for improving the dimensional stability of the photographic element are, e.g., dispersions of a water-soluble or hardly soluble synthetic polymer, e.g., polymers of alkyl(meth) acrylates, alkoxy(meth) acrylates, glycidyl (meth) acrylates, (meth) acrylamides, vinyl esters, acrylonitriles, olefins, and styrenes, or copolymers of the above with acrylic acids, methacrylic acids, $\alpha$-$\beta$-unsaturated dicarboxylic acids, hydroxyalkyl (meth) acrylates, sulphoalkyl (meth)acrylates, and styrenesulphonic acids.

Suitable UV-absorbers are, e.g., aryl-substituted benzotriazole compounds as described in U.S. Pat. No. 3,533,794, 4-thiazolidone compounds as described in U.S. Pat. Nos. 3,314,794 and 3,352,681, benzophenone compounds as described in JP-A 2784/71, cinnamic ester compounds as described in U.S. Pat. Nos. 3,705,805 and 3,707,375, butadiene compounds as described in U.S. Pat. No. 4,045,229, and benzoxazole compounds as described in U.S. Pat. No. 3,700,455. UV-absorbers are especially useful in colour materials where they prevent fading by light of the colour images formed after processing.

Spacing agents can be present of which, in general, the average particle size is comprised between 0.2 and 10 μm. They may be soluble or insoluble in alkali. Alkali-insoluble spacing agents usually remain permanently in the photographic element, whereas alkali-soluble ones usually are removed therefrom in an alkaline processing bath. Suitable spacing agents can be made, e.g., of polymethyl methacrylate, of copolymers of acrylic acid and methyl methacrylate, and of hydroxypropylmethylcellulose hexahydrophthalate. Other suitable spacing agents have been described in U.S. Pat. No. 4,614,708.

The photographic material may contain several non-light-sensitive layers, e.g., an antistress topcoat, one or more backing layers, and one or more intermediate layers optionally containing filter- or antihalation dyes that absorb scattered light and thus promote the image sharpness. Suitable light-absorbing dyes used in these intermediate layers are described in, e.g., U.S. Pat. Nos. 4,092,168 and 4,311,787, DE-P 2,453,217, and GB-P 7,907,440. When these dyes are incorporated in such an intermediate layer between the emulsion layer(s) and the support, there will be only a negligeable loss in sensitivity, but in rapid processing conditions decolouration of the filter dyes may form an additional problem. A solution therefor may be found by decreasing the thickness of the entire layer packet.

One or more backing layers can be applied to the non-light-sensitive side of the support of materials coated with at least one emulsion layer at only one side of the support. These layers, which can serve as anti-curl layer, may contain, e.g., matting agents like silica particles, lubricants, antistatic agents, light-absorbing dyes, opacifying agents, e.g. titanium oxide, and the usual ingredients like hardeners and wetting agents.

The support of the photographic material may be opaque or transparent, e.g. a paper support or resin support. When a paper support is used preference is given to one coated at one or both sides with an $\alpha$-olefin polymer, e.g. a polyethylene layer, which optionally contains an anti-halation dye or pigment. It is also possible to use an organic resin support, e.g., cellulose nitrate film, cellulose acetate film, poly(vinyl acetal) film, polystyrene film, poly(ethylene terephthalate) film, polycarbonate film, poly(vinyl chloride) film or poly-$\alpha$-olefin films such as polyethylene or polypropylene film. The thickness of such organic resin film is preferably comprised between 0.07 and 0.35 mm. These organic resin supports are preferably coated with a subbing layer, which may contain water insoluble particles such as silica or titanium dioxide.

The photographic material according to the present invention can be image-wise exposed by any convenient radiation source used for its specific application.

Of course, processing conditions and the composition of processing solutions depend on the specific type of photographic material in which the silver halide grains and the compounds according to the general formula (I) according to the present invention are applied. For example, the specific photographic material according to a preferred embodiment is a material for X-ray diagnostic purposes adapted to rapid processing conditions. Therefor preferably an automatically operating processing apparatus is used provided with a system for the automatic regeneration of the processing solutions. The prehardened material may be processed with one-part package chemicals or three-part package chemicals, depending on the processing application determining the degree of hardening required in said processing cycle.

Applications within total processing times of up to 90 seconds, known as common practice, are possible, but according to this invention processing in rapid processing cycles of less than 60 seconds dry-to-dry by the steps of developing, fixing, rinsing and drying can be obtained, even with low regeneration amounts for developer and/or fixer.

Processing a photographic material according to this invention may be performed in any suitable well-known developer and fixer used for the said photographic materials, but a preferred processing method for X-ray photographic materials has, e.g., been described in EP-Application No. 542 354.

Preferably, in accordance with this invention development proceeds in a developer comprising 4-hydroxymethyl-4-methyl-l-phenyl-3-pyrazolidin-1-one as an auxiliary developing agent in addition to hydroquinone as main developing agent.

From an ecological point of view it is preferable to replace completely or part of the ammonium thiosulphate by sodium thiosulphate in the fixing solution. Preferred amounts of sodium thiosulphate are in the range of at least 200 g/l in a fixer ready-for-use.

Besides the use in radiographic materials the compounds according to the general formula (I) in connection with the present invention can be used in various types of photographic elements, e.g. black-and-white silver halide photographic materials, like materials for graphic or micrographic applications, or colour materials. The photographic element may contain one single emulsion layer, or it can be built up by two or even more emulsion layers. In colour photography the material contains blue-, green- and red-sensitive layers each of which can be single coated, but normally consists of double or even triple layers. According to this invention a particularly preferred photographic material is a colour photographic material coated with at least one blue-sensitive, at least one green-sensitive, at least one red-sensitive silver halide emulsion layer, at least one intermediate layer between the colour sensitive layers and at least one afterlayer on one side of the support, wherein at least one layer comprises at least one compound corresponding to the general formula (I).

An advantageous aspect related to this invention is the presence of the chemical compounds in the photographic material according to this invention. As opposed to the amount of the same compounds in the processing solutions, the amount required in the layer(s) of the silver halide photographic material is much less, thus leading to a less expensive manufacture of it.

In a preferred embodiment, the material comprises flat bromoiodide tabular grain emulsions with an average grain thickness of less than 0.30 μm and an average aspect ratio of at least 2:1. The products used herein have an activating effect resulting in an enhanced speed and contrast and in improved keeping properties.

The following examples illustrate the invention without however limiting it thereto.

EXAMPLES

Example 1

A photographic colour negative film element was produced comprising a transparent film support and coated thereon in succession with:

—a subbing layer,

—a blue antihalation layer comprising a blue non-diffusing pentamethine oxonol-type barbituric acid derivative dye in dispersed state in a hydrophilic colloid, absorbing red light and being removable and/or decolourisable in a processing bath, —a low-sensitive and a high-sensitive red-sensitised silver halide emulsion layer each comprising a cyan-forming coupler, —an intermediate layer, a low-sensitive and a high-sensitive green-sensitized silver halide emulsion layer each comprising a magenta-forming coupler, —a yellow filter layer, —a low-sensitive and a high-sensitive blue-sensitive silver halide emulsion layer each comprising a yellow-forming coupler, —an antistress layer, and —an afterlayer for the dosage of the hardener.

Samples of colour negative film elements A to I were made. All samples had an identical composition except for the compound added to the afterlayer.

The amounts of gelatin present in the afterlayer and in the protective antistress layer were 0.40 g and 1.45 g per m² respectively. An amount of 2.5 mg of compound as indicated in Table 1 was added per m² to the afterlayer just before coating. The total amount of gelatin coated as a binder in the colour negative film samples was 15.05 g per m². A total amount of 50±3 g of water per m² was absorbed by each sample after dipping in demineralized water of 25° C. the sample for 3 minutes before processing.

Each of the samples A to I was individually placed in contact with a transparent wedge and exposed to blue monochromatic light. After colour development, the values of speed of the blue sensitive layer were measured at a density of 0.2 above fog. They are also listed in Table 1.

The values 0 and 100, given to element A for fog and speed are relative values, the value of +1 indicating a fog increase of the density with 0.01; the value 200 corresponding to a doubling of the speed. Moreover the fog values are given for the materials after storage for 3 days in an atmosphere having a temperature of 57° C. and a relative humidity of 34% to simulate the behaviour after storage.

The formulae of the comparative compounds CMP-1 to CMP-3, known from DE PS2 360 878 with n varying from 10 to 15, are given below.

—Comparative compound CMP-1: 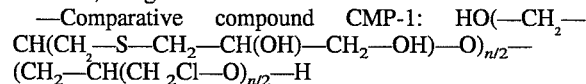

—Comparative compound CMP-2: 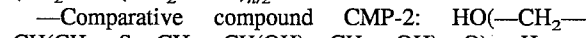

—Comparative compound CMP-3: 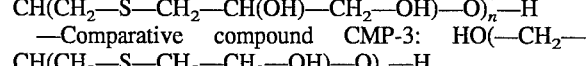

The results summarised in Table 1 demonstrate that the compounds according to the present invention added to the non-light-sensitive afterlayer of a colour negative material lead to an increase in sensitivity with a tolerable increase in fog, even after storage of the material.

TABLE 1

| Material | Compound | Fog | Sensitivity | Fog 3d 57/34 |
|---|---|---|---|---|
| A | No | 0 | 100 | +5 |
| B | CMP-1 | 0 | 101 | +8 |
| C | CMP-2 | +2 | 101 | +10 |
| D | CMP-3 | +1 | 101 | +11 |
| E | C-1 | +1 | 103 | +4 |
| F | C-2 | +2 | 104 | +4 |
| G | C-3 | +1 | 103 | +5 |
| H | C-4 | +1 | 106 | +5 |
| I | C-7 | +1 | 105 | +5 |

Example 2

A photographic colour negative film element was produced comprising a transparent film support and coated thereon in succession with:

—a subbing layer,

—a antihalation layer comprising black colloidal silver,

—a low-sensitive red-sensitised silver halide emulsion layer comprising a cyan-forming coupler (silver iodide content of the silver halide emulsion: 6 mole %), —a medium-sensitive red-sensitised silver halide emulsion layer comprising a cyan-forming coupler (silver iodide content of the silver halide emulsion: 7 mole %), —a high-sensitive red-sensitised silver halide emulsion layer comprising a cyan-forming coupler (silver iodide content of the silver halide emulsion: 10 mole %), —an intermediate layer, —a low-sensitive green-sensitized silver halide emulsion layer comprising a magenta-forming coupler (silver iodide content of the silver halide emulsion: 5 mole %), —a medium-sensitive green-sensitized silver halide emulsion layer comprising a magenta-forming coupler (silver iodide content of the silver halide emulsion: 6 mole %), —a high-sensitive green-sensitized silver halide emulsion layer comprising a magenta-forming coupler (silver iodide content of the silver halide emulsion: 9 mole %), —an intermediate layer, —a yellow filter layer, —a low-sensitive blue-sensitive silver halide emulsion layer comprising a yellow-forming coupler (silver iodide content of the silver halide emulsion: 6 mole %), —a high-sensitive blue-sensitive silver halide emulsion layer comprising a yellow-forming coupler (silver iodide content of the silver halide emulsion: 11 mole %), —an antistress layer, and —an afterlayer for the dosage of the hardener.

Samples of colour negative film elements A to I were made. All samples had an identical composition except for the compound added to the intermediate layer adjacent to the high-sensitive red-sensitised silver halide emulsion layer.

An amount of 2 mg/m² of the compound as indicated in Table 3 was added to the intermediate layer just before coating.

Each of the samples A to I was individually placed in contact with a transparent wedge and exposed to white light. After colour development, the values of speed of the red sensitive layer were measured at a density of 0.2 above fog. They are listed in Table 2.

The values 0 and 100, given to element A for fog and speed, are relative values, the value of +1 indicating a fog increase of the density with 0.01; the value 200 corresponding to a doubling of the speed. Moreover the fog values are given for the materials after storage for 3 days in an atmosphere having a temperature of 57° C. and a relative humidity of 34% to simulate the behaviour after storage.

The comparative compounds CMP-1 to CMP-3 are the same as those given in Example 1.

The results summarised in Table 2 demonstrate that the compounds according to the present invention added to the non-light-sensitive intermediate layer adjacent to the high-sensitive red-sensitised silver halide emulsion layer of a colour negative material lead to an increase in sensitivity with a tolerable increase in fog, even after storage of the material.

TABLE 2

| Material | Compound | Fog | Sensitivity | Fog 3d 57/34 |
|---|---|---|---|---|
| A | No | 0 | 100 | +3 |
| B | CMP-1 | +1 | 102 | +10 |
| C | CMP-2 | +1 | 101 | +9 |
| D | CMP-3 | +2 | 101 | +12 |
| E | C-1 | +1 | 112 | +4 |
| F | C-3 | +2 | 110 | +6 |
| G | C-4 | +1 | 111 | +5 |
| H | C-5 | +3 | 111 | +6 |
| I | C-6 | +1 | 109 | +5 |

Example 3

A. Description of double-side coated X-ray materials X1-X6

Emulsion preparation

A tabular silver bromoiodide emulsion, containing 1 mole % of AgI and 99 mole % of AgBr, was precipitated by the double-jet technique. The obtained emulsion, containing 75 g of gelatin per mole of $AgNO_3$, had the following characteristics:

—mean diameter of the circle with the same projective surface of the tabular grain: 1.37+/–0.38 μm (0.28 as the standard variation s).

—mean thickness of the tabular grains: 0.22 μm.

—mean aspect ratio: 6.32.

—percentage of total projective surface area covered by the tabular grains: 98%.

Chemical sensitisation

This emulsion was chemically sensitised with 660 mg of dye 1 (anhydro- 5,5'-dichloro-3,3'-bis(n-sulphobutyl)-9-ethyloxacarbocyanine hydroxide), and optimal amounts of chloroauric acid, sodium thiosulphate, and potassium thiocyanate per mole of $AgNO_3$ to attain a good relationship between fog and sensitivity.

Preparation of the emulsion coating solution

The following ingredients were added per mole of silver halide:

| | |
|---|---|
| 4-hydroxy-6-methyl-1,3,3a,7-tetraazaindene: | 0.29 g |
| sorbitol | 9.10 g |
| poly(ethyl acrylate) (MW = 1000000) | 14.50 g |
| 1,3 dihydroxybenzene | 3.05 g |
| dextrane (MW = 10000) | 31.00 g |

Composition of the protective layer
The coating weight is expressed in g/m² per side

| | |
|---|---|
| gelatin | 1.10 |
| poly(methyl methacrylate) (average particle diameter: 3.5 μm) | 0.023 |
| formaldehyde | 0.1 |

Coating of material X1

Both the emulsion layer and the protective layer were simultaneously coated on both sides of a blue poly(ethylene terephthalate) film support of 175 μm thickness. The resulting photographic material contained an amount of silver halide corresponding to 3.5 g of $AgNO_3$ per m² per side.

Coating of materials X2—X6

Same materials as material X1, except for the compounds that were added to the protective layer composition in an amount of 10 mg/m² per side.

B. Exposure, sensitometry and densitometry

Samples of the photographic materials 1 to 4 were exposed through a continuous wedge with green light of 540 nm for 0.02 s and were processed under the circumstances described below. The density was measured as a function of the light dose and therefrom were determined: fog level (Fog Dens.) measured as density with an accuracy of 0.001, the relative speed (Speed) at a density of 1 above fog (material 1 was set to a speed of 100) and the Average Gradient measured between the densities 0.25 above fog and 2.0 above fog.

C. Processing conditions and composition of processing chemicals

—processing machine: CURIX 402 (trademarked name of Agfa-Gevaert) with the following time (in seconds (s)) and temperature (in ° C) and processing chemicals characteristics of:

| | |
|---|---|
| loading | 3.4 s |
| developing | 23.4 s 35°C.; developer AGFA G138 (trade name) |
| cross-over | 3.8 s |
| fixing | 15.7 s 35°C.; fixer AGFA G334 (trade name) |
| cross-over | 3.8 s |
| rinsing | 15.7 s 20°C. |
| drying | 32.2 s |
| total | 98.0 s |

D. Results

Table 3 gives fog, speed, and average gradient values of materials X1-X6 after processing in the above-described processing cycle.

TABLE 3

| Material | Compound | Fog Dens. | Speed | Average Gradient |
|---|---|---|---|---|
| X1 | No | 0.013 | 100 | 2.94 |
| X2 | C-1 | 0.013 | 75 | 3.17 |
| X3 | C-2 | 0.015 | 120 | 3.37 |
| X4 | C-3 | 0.016 | 120 | 3.32 |
| X5 | C-4 | 0.022 | 100 | 3.40 |
| X6 | C-7 | 0.048 | 143 | 3.32 |

Table 3 shows the activating effect of compounds C-2, C-3 and C-7 resulting in a higher speed and a clearly higher average gradient with an acceptable increase of fog.

We claim:

1. Photographic material comprising on at least one side of a support at least one light-sensitive silver halide emulsion layer, one or more intermediate layer(s) and an antistress topcoat, characterized in that the said material comprises at least one compound having the general formula (I)

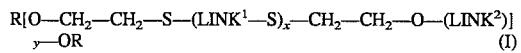

$$R[O-CH_2-CH_2-S-(LINK^1-S)_x-CH_2-CH_2-O-(LINK^2)]_y-OR \quad (I)$$

wherein each of $LINK^1$ and $LINK^2$ which may be the same or different represents a divalent linking group;

R represents H, an alkyl group, an aryl group or an acyl group;

x is 0, 1 or 2, and y varies from 2 to 20.

2. Photographic material according to claim 1, wherein in the compound having the general formula (I) $LINK^1$ and/or $LINK^2$ is a divalent group selected from the group consisting of $-CH_2-CH_2-$; $-CH_2-CH_2-O-CH_2-CH_2-$; $(CH_2-CH_2-O)_n-CH_2-CH_2$ with n=2, 3 or 4; $-CH_2-CH_2-CH(CH_3)_2-CH_2-CH_2-$; $-CH_2-CH_2-NH-CO-NH-CH_2-CH_2-$; $-CH_2-CH_2-C(R^1)(R^2)-CH_2-$; $-CH_2-CH_2-N(COR^3)-CH_2-CH_2-$; $-CH_2-CH_2-NR^4-CH_2-CH_2-$; $-CH_2-Phen-CH_2-$; $-CH_2-CH_2-NH-CO-CO-NH-CH_2-CH_2-$ wherein Phen represents phenyl and each of $R^1$, $R^2$, $R^3$ and $R^4$ independently represents H, a substituted or unsubstituted alkyl group or a substituted or unsubstituted aryl group.

3. Photographic material according to claim 1, wherein the compound (I) is present in an amount of 0.1 to 20 mg per $m^2$ and per side of the support.

4. Photographic material according to claim 1, wherein the silver halide has been spectrally sensitised with anhydro-5,5'-dichloro-3,3'-bis(n-sulphobutyl)-9-ethyloxacarbocyanine hydroxide or anhydro-5,5'-dichloro-3,3'-bis(n-sulfopropyl)-9-ethyloxacarbo-cyanine hydroxide.

5. Photographic material according to claim 1, wherein the silver halide is silver bromoiodide, silver chlorobromoiodide, silver chloroiodide, silver chlorobromide, silver bromide or silver chloride or a mixture thereof.

6. Photographic material according to claim 1, wherein said material is a photographic X-ray material coated with light-sensitive layers at both sides of the support.

7. Photographic material according to claim 1, wherein said material is coated with at least one light-sensitive layer comprising flat bromoiodide tabular grain emulsions having an average grain thickness of less than 0.30 μm and an average aspect ratio of at least 2:1.

8. Photographic material according to claim 1, wherein said material is a colour material coated with at least one blue-sensitive, at least one green-sensitive, at least one red-sensitive layer, at least one intermediate layer and at least one afterlayer wherein at least one of said layers comprises at least one compound according to general formula (I).

* * * * *